United States Patent [19]
Liebert et al.

[11] Patent Number: 5,314,415
[45] Date of Patent: May 24, 1994

[54] ASPIRATING PLUNGER FOR POWER INJECTOR CARTRIDGES

[75] Inventors: Richard T. Liebert, Ballston Spa, N.Y.; Neil H. Brown, Royersford, Pa.

[73] Assignee: Sterling Winthrop Inc., Malvern, Pa.

[21] Appl. No.: 94,284

[22] Filed: Jul. 21, 1993

[51] Int. Cl.⁵ ............................................. A61M 5/315
[52] U.S. Cl. ..................................... 604/218; 604/228
[58] Field of Search .......................... 604/110, 218–229

[56] References Cited

U.S. PATENT DOCUMENTS

| | | |
|---|---|---|
| Re. 32,974 | 7/1989 | Porat et al. |
| 1,222,424 | 4/1917 | Laurent. |
| 1,707,880 | 4/1929 | Sheets. |
| 1,799,463 | 4/1931 | Hein ............................... 604/222 X |
| 3,045,674 | 7/1962 | Goldberg ........................ 604/229 X |
| 3,669,111 | 6/1972 | Dubner. |
| 3,705,582 | 12/1972 | Stumpf et al. |
| 3,766,918 | 10/1973 | Kessel. |
| 3,834,387 | 9/1974 | Brown. |
| 3,939,833 | 2/1976 | Hansson et al. ................. 604/218 X |
| 4,216,771 | 8/1980 | Arlers et al. |
| 4,299,238 | 11/1981 | Baidwan et al. |
| 4,333,457 | 6/1982 | Margulies. |
| 4,685,910 | 8/1987 | Schweizer ........................... 604/218 |
| 4,874,372 | 10/1989 | McArthur et al. ................. 604/110 |
| 4,911,695 | 3/1990 | Lindner ............................. 604/228 |
| 4,973,308 | 11/1990 | Borras et al. ..................... 604/110 |
| 5,000,735 | 3/1991 | Whelan ............................. 604/110 |
| 5,007,904 | 4/1991 | Densmore et al. ................. 604/228 |
| 5,106,372 | 4/1992 | Ranford ............................ 604/110 |
| 5,176,639 | 1/1993 | Pozzi et al. ....................... 604/110 |
| 5,201,709 | 4/1993 | Capra et al. ...................... 604/110 |
| 5,201,710 | 4/1993 | Caselli ............................... 604/110 |

*Primary Examiner*—John D. Yasko
*Assistant Examiner*—Adam J. Cermak
*Attorney, Agent, or Firm*—Imre (Jim) Balogh; Arthur Rosenstein

[57] ABSTRACT

A self-aspirating plunger for power injector cartridges characterized by its ability to pump head space gas and aspirate the power injector cartridge without the need to draw backward on the plunger toward the proximal end of the cartridge comprising:

a female ring component;

a male component having a stem and a cone-shaped portion, said stem slideably fitting into said female ring component; and an elastomeric diaphragm shell covering said female ring component and said cone shaped head portion of said male component.

6 Claims, 4 Drawing Sheets

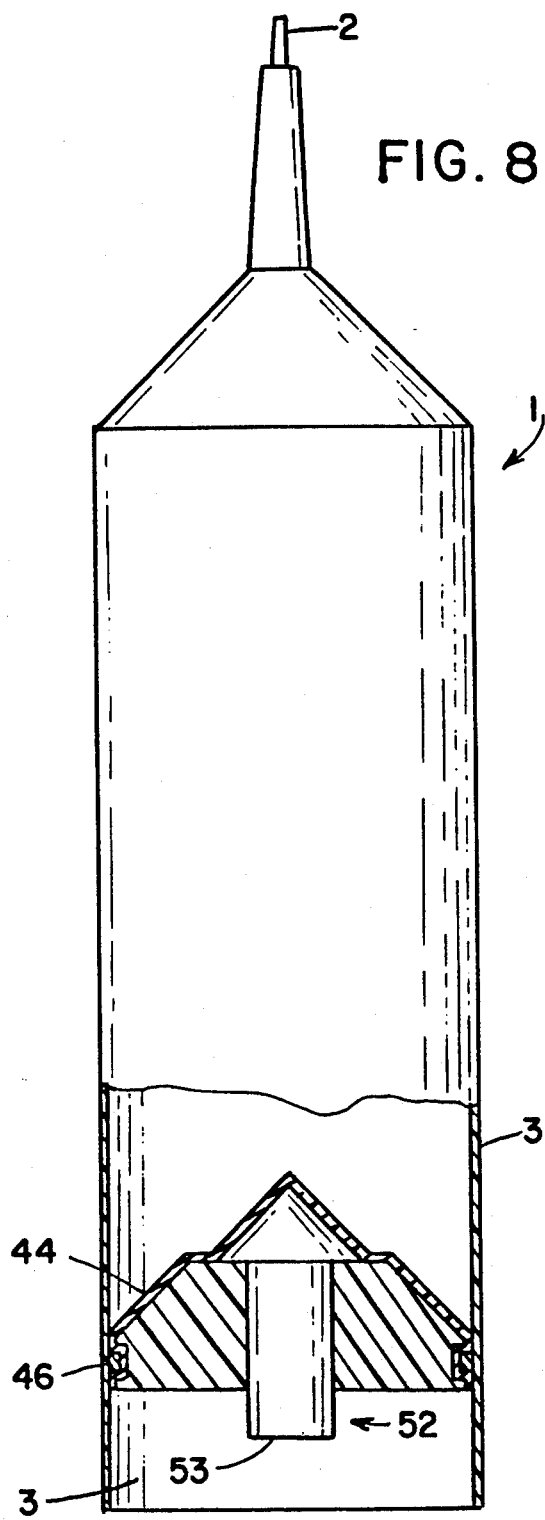
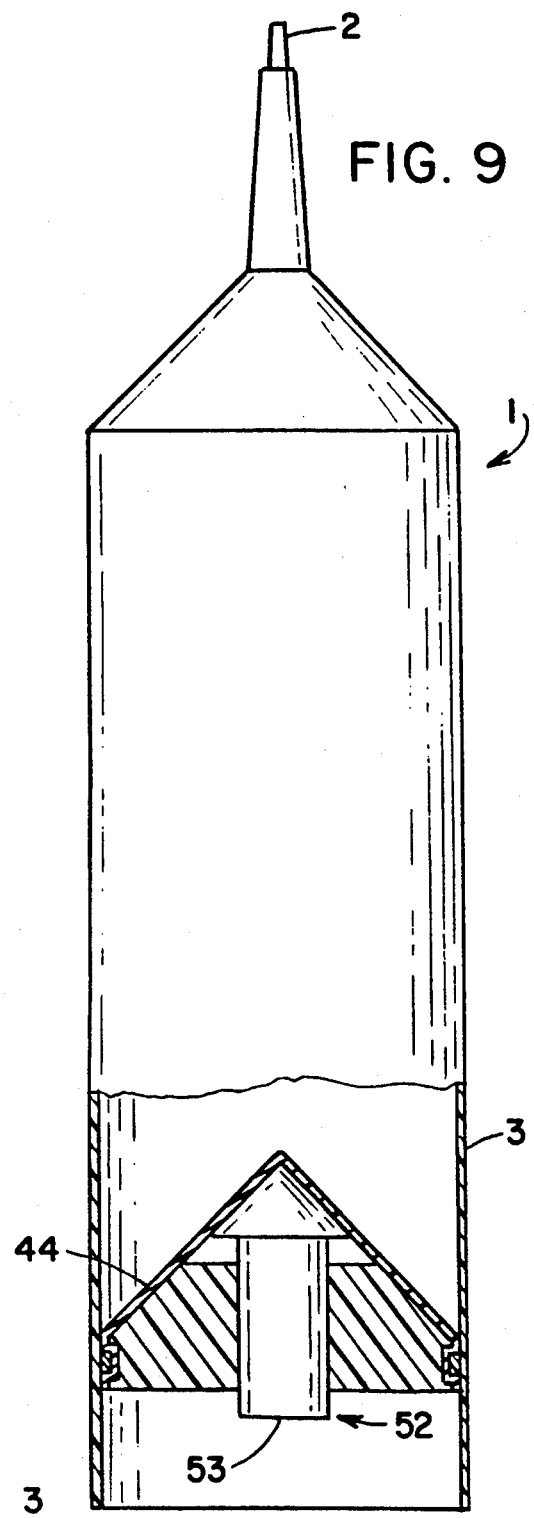

ASPIRATING PLUNGER FOR POWER INJECTOR CARTRIDGES

BACKGROUND OF THE INVENTION

1. Field of the Invention

This invention relates to syringes which are utilized either for the introduction or withdrawal of fluids to and from a patient. More particularly, this invention relates to power aspirating plungers with aspirating effect used in conjunction with power injectors to deliver liquid imaging agents into the body of a patient.

2. Reported Developments

In medical practice, hypodermic injections are sometimes administered subcutaneously, while others must be given intravenously, depending upon the particular medication to be administered. In either case, it is essential that the practitioner know with certainty, prior to injection of the medication whether the hypodermic needle tip is located in a major blood vessel, such as a vein, or in subcutaneous tissue. Use of an aspirating syringe in which a negative pressure can be generated in the syringe affords a means of making such determination. Thus the appearance of blood in the syringe upon generation of the negative pressure would indicate location of the needle tip in a major blood vessel, while the lack of appearance of blood would indicate location of the tip in subcutaneous tissue. Depending upon the type of injection intended, the injection can then either proceed directly, or if appropriate the tip can be withdrawn and relocated.

Aspirating syringes are generally of two types, namely, they are either manually or automatically aspirated. In the manually aspirated type the plunger is retracted for a short distance within the barrel of the syringe. This retraction lowers the pressure within the syringe which leaves fluids at the needle tip which are then observable within the barrel of the syringe. From solid tissues no fluids will be drawn into the barrel. In the manually aspirated syringes the injection necessitates the use of both hands, one to hold the barrel, and the other to exert pressure in a rearward direction on the plunger. Such manually actuatable aspirating syringes have the disadvantage that their proper use depends on very large measure on the degree of skill of the person administering the injections.

Aspiration in syringes of the automatic or self-aspirating type is effected by first inducing a positive pressure in a medicament-containing portion of the syringe, for example in a disposable cartridge ampoule. On release of the force inducing the positive pressure, a corresponding negative pressure in the syringe is generated thus giving rise to the aspirating effect. The present invention relates to this self-aspirating type syringes.

Ideally a self-aspirating hypodermic syringe should be relatively simple in construction so as to minimize the cost of production; should be relatively simple to operate; should be capable of manipulation with one hand; should be adaptable to multiple self-aspirating actions; should be capable of expelling trapped air from the ampoule prior to insertion of the needle into the injection site and prior to initiation of the self-aspirating action without either precluding self-aspirating action at a later time in the operation sequence of the syringe or otherwise rendering it inoperative.

The self-aspirating syringes provided by the present invention mimic, automatically, the slight rearward piston displacement withdrawal action of manually operable syringes, thus generating the slight negative pressure in the syringes essential for aspiration. The syringes of the present invention therefore obviate the disadvantage inherent in prior art syringes of the manual type, since the aspirating action is generated automatically which requires no special skill on the part of the practitioner.

SUMMARY OF THE INVENTION

In accordance with the present invention there is provided an aspirating plunger, preferably used in power injector cartridges, characterized by its ability to purge headspace gas and then aspirate the power injector cartridge without the need to draw backward on the plunger toward the proximal end of the cartridge.

The aspirating plunger of the present invention comprises:
- a female ring component;
- a male component having a stem and a cone-shaped portion, said stem slideably fitting into said female ring component; and
- an elastomeric diaphragm shell covering said female ring component and said cone shaped head portion of said male component.

The female ring component is a generally cone-shaped component having a vertically oriented cylindrical hole bored through the center thereof, with the pointed end of the cone cut off, fabricated from a rigid material. The particular configuration of the female ring component includes: a cylindrical flat, bottom portion so as to conform to the cylindrical shape of the power injector cartridge; spaced from said cylindrical bottom portion there is provided a cylindrical groove to receive and retain the diaphragm shell; a flat cylindrical top portion spaced from the cylindrical groove portion; and a side portion, connecting said cylindrical bottom and top portions and integral therewith, said side portion having a degree of incline with respect to a horizontal plane of from about 1° to about 89°, preferably of from about 30° to 60°, and most preferably of about 45°.

The male component is mushroom-shaped, fabricated from a rigid polymeric material, having a cylindrical plunger shaft with an outside diameter (OD) smaller than the inside diameter (ID) of the female ring component so that the shaft will slideably fit into the hole of the female ring and a cone-shaped head at one end of the shaft and integral therewith, having a flange the OD of which is larger than the ID of the hole in the female ring component, said cone shaped head having a degree of incline with respect to a horizontal plane of from about 1° to about 89°, preferably of from about 30° to 60°, and most preferably of about 45°.

It is preferred that upon assembly, the head portion of the male component and the side portion of the female component form a continuous cone-shaped assembly, where the OD of the flat top portion of the female ring component is the same as the OD of the flange of the male component.

The most preferred configuration of the male and female components assembly comprises: matching head portion of the male component with the female component forming a continuous cone-shaped plunger head wherein the side of the cone forms about a 45° angle with a horizontal plane.

A low friction sliding fit is desirable between the shaft of the male component and the wall of the female ring component for easy operation thereof.

The third component of the aspirating plunger is an elastomeric diaphragm shell or sheath having a cylindrical bottom portion and a generally cone-shaped side portion integral therewith. It is designed to cover the assembled male and female components, the side portion serving as diaphragm therefor and the cylindrical bottom portion as a slideable seal between the rigid female component of the aspirating plunger and the wall of the power injector cartridge. The cylindrical bottom portion of the diaphragm shell includes an inwardly protruding protuberance to engage the cylindrical groove on the bottom of the female ring component.

It is essential to have a high frictional sliding seal between the cylindrical portion of the diaphragm shell and the wall of the power injector cartridge to prevent leakage of the content therefrom.

In using the assembled plunger contained in the power injector cartridge for expelling head space gas and aspirating, force is applied to the plunger shaft in the direction of the orbital end of the cartridge to move the male component within the female component and thereby urging the side portion of the diaphragm shell to extend. The elastic extension/deformation of the diaphragm reduces the head space expelling the head space gas; upon disengaging the force exerted on the shaft, the diaphragm repairs its original shape by virtue of its elastic memory, and negative gauge pressure is generated in the closed system resulting in the process of aspirating.

After the aspirating process is completed, force is further exerted on the plunger shaft by activating the power injector. The force will move the plunger assembly towards the orbital end of the cartridge to deliver the fluid content from the cartridge to the sight of the injection.

In the aspirating plunger/injector cartridge it is absolutely essential that the force required to move the aspirating plunger in the power injector cartridge exceeds the force required to aspirate the plunger.

BRIEF DESCRIPTION OF THE DRAWINGS

FIG. 8 is a cross-sectional elevational view of the aspirating plunger seated in the power injector cartridge in a static rest configuration.

FIG. 9 is a cross-sectional elevational view of the aspirating plunger seated in the power injector cartridge in a dynamic bleed-aspirate configuration.

DETAILED DESCRIPTION OF THE INVENTION

It is to be noted that the present invention accomplishes aspiration in a manner not resembling prior art described devices that require the plunger rod to have a locking connection with the plunger for the purpose of aspiration. The present invention accomplishes aspiration as a function of its design, i.e. without the need of drawing the plunger toward the proximal end of the cartridge.

Reference is now made to the drawings in describing the aspirating plunger of the present invention.

Figure 1:
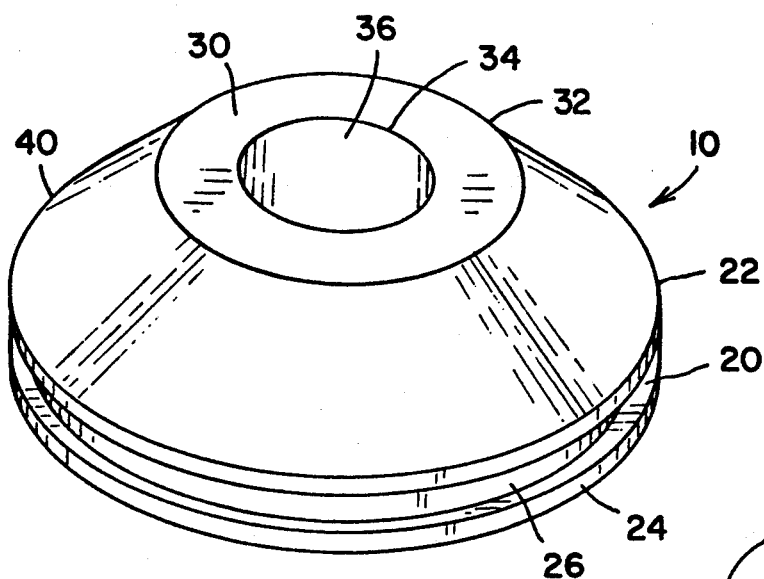
FIG. 1 is a perspective view of the female ring component of the aspirating plunger.

FIG. 1 shows the female ring component of the plunger generally designated at 10, which is fabricated from a rigid material, such as plastic and includes cylindrical bottom portion 20, flat top portion 30, and conical side portion 40.

Figure 4:
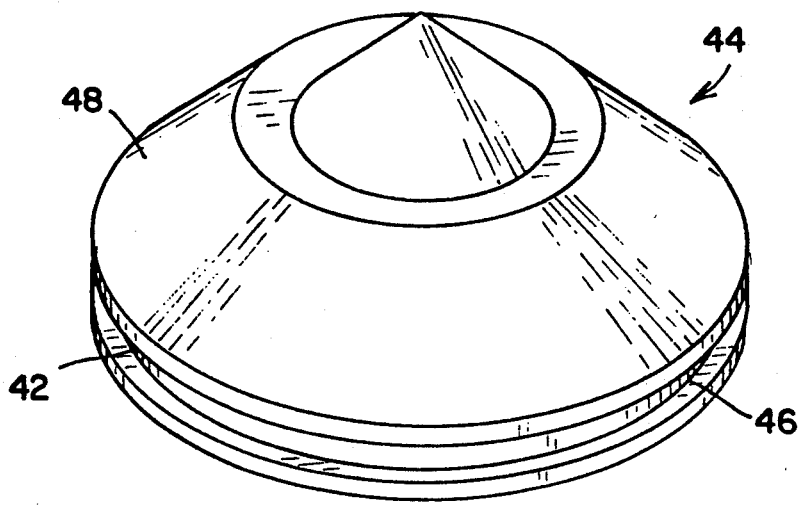
FIG. 4 is a perspective view of the elastomeric diaphragm shell.
Figure 5:
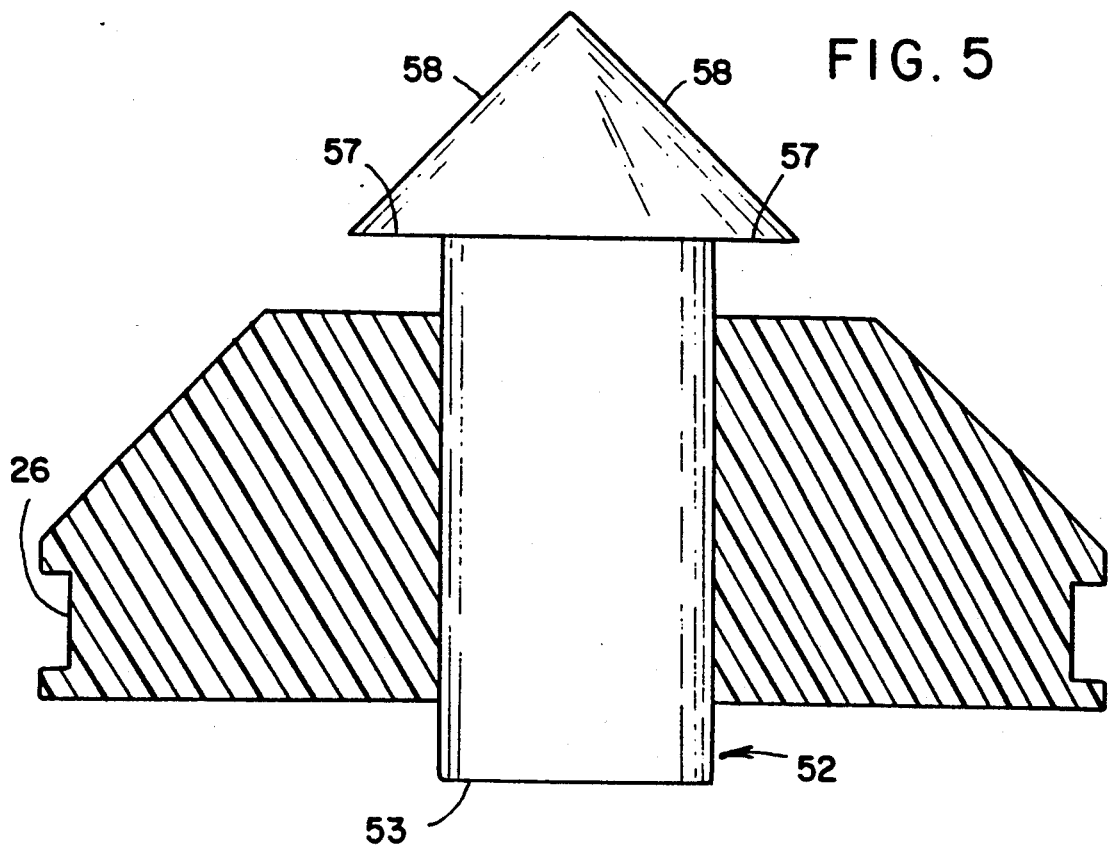
FIG. 5 is a cross-sectional elevational view of the female ring component of FIG. 1 and male component of FIG. 2 showing male component in an extended position.

Cylindrical bottom portion 20 comprises top annular rim 22 and bottom annular rim 24 and recess or groove 26 therebetween which serves to receive and retain diaphragm-shell generally designated at 44 in FIG. 4. Flat top portion 30, spaced from cylindrical bottom portion 20, is defined by first annular rim 32 and second annular rim 34. Connecting top annular rim 22 of cylindrical bottom portion 20 and first annular rim 32 is side portion 40, which may have a degree of incline with respect to a horizontal plane of from about 1 degree to about 89 degree, preferably of from about 30 degree to 60 degree, and most preferable of about 45 degree. The degree of incline is determined by the respective diameters of first annular rim 32 and top annular rim 22 of cylindrical bottom of portion 20. Vertically oriented cylindrical hole 36 is defined by the diameter of second annular rim 34.

Figure 2:
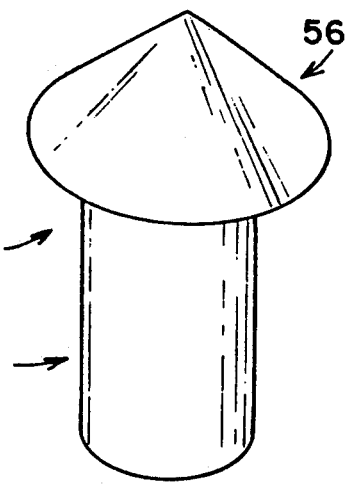
FIG. 2 is a perspective view of the male component of the aspirating plunger.

FIG. 2 shows the generally mushroom shaped male component, denoted at 50, of the aspirating plunger of the present invention, which is also fabricated from a rigid material, such as plastic, which comprises: a solid cylindrical plunger shaft 52, and cone shaped head 56.

Figure 3:
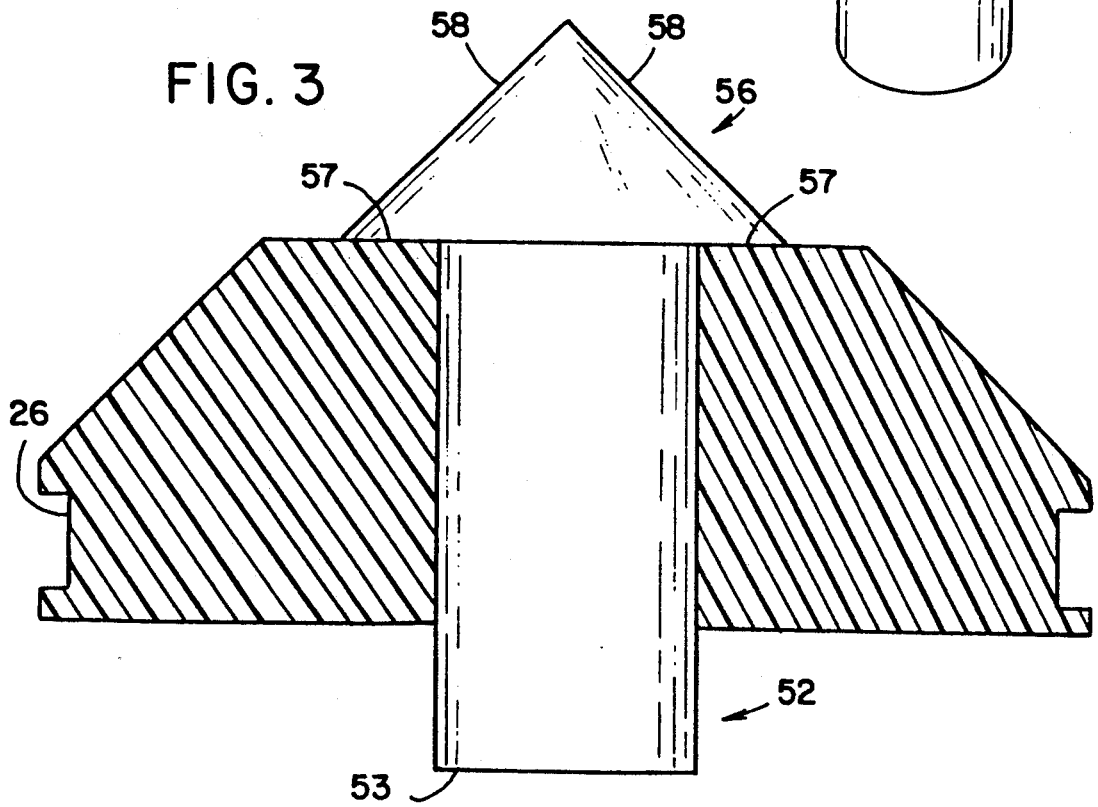
FIG. 3 is a cross-sectional elevational view of the female ring component of FIG. 1, and male component of FIG. 2 assembly, in a static rest configuration.

Referring to FIGS. 1, 2 and 3, the diameter 53 of the plunger shaft 52 is smaller than the diameter of the second annular rim 34, so that a slideable fit is provided therebetween. Cone-shaped head 56 having flange 57 and side 58 overlaps flat top portion 30 of female ring component 10. Flange 57 should be just sufficiently larger than the diameter of second annular rim 34; flange 57 may extend outside the first annular rim 32, however, it should not reach the diameter of top annular rim 22 of cylindrical bottom portion 20.

Figure 6:
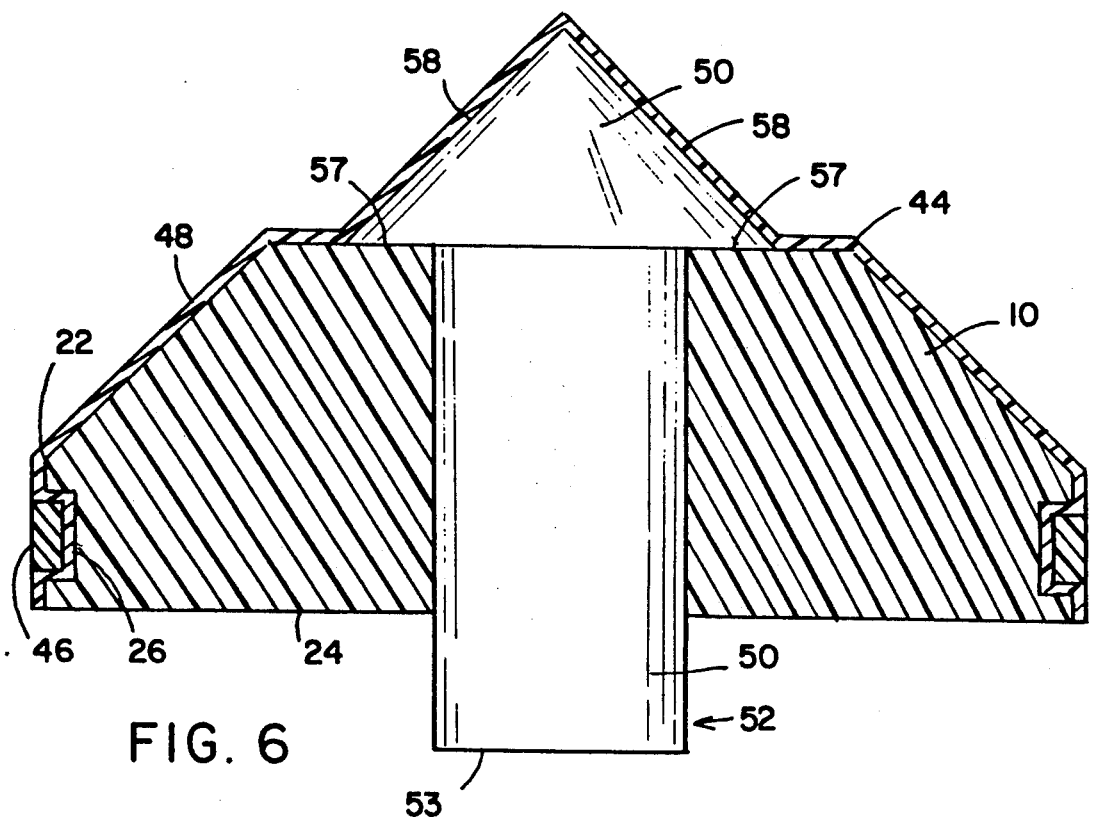
FIG. 6 is a cross-sectional elevational view of the assembled aspirating plunger in a static rest configuration.

The third component of aspirating plunger of the present invention is a diaphragm-shell shown at 44 in FIGS. 4 and 6. It is fabricated from a high elastomeric memory material and is inert in contact with liquid medicinals and diagnostic agents. Diaphragm-shell 44 comprises cylindrical bottom portion 42 and a generally cone shaped side portion 48. Cylindrical bottom portion 42 comprises annular protuberance 46 facing toward the center of diaphragm-shell 44 that tightly fits into grove 26 of female ring component 10. The configuration of diaphragm-shell 44 closely resembles the configuration of assembled male and female components of the aspirating plunger.

Upon assembling the aspirating plunger of the present invention, male component 50 (FIG. 2) is fitted into female ring component 10 (FIG. 1). FIG. 3 shows the two components fitted together in a static rest position, position in which male component 50 is extended upward, i.e. its head portion 56 is spaced from flat top portion 30 of female ring component 10.

FIG. 6 shows the three parts of the aspirating plunger assembled and in a static rest position. Diaphragm-shell 44 covers head portion 58 of male component 50 and female ring component 10. Annular protuberance 46 of diaphragm-shell 44 tightly fits into groove 26 of cylindrical bottom portion 20 of female ring component 10.

Figure 7:
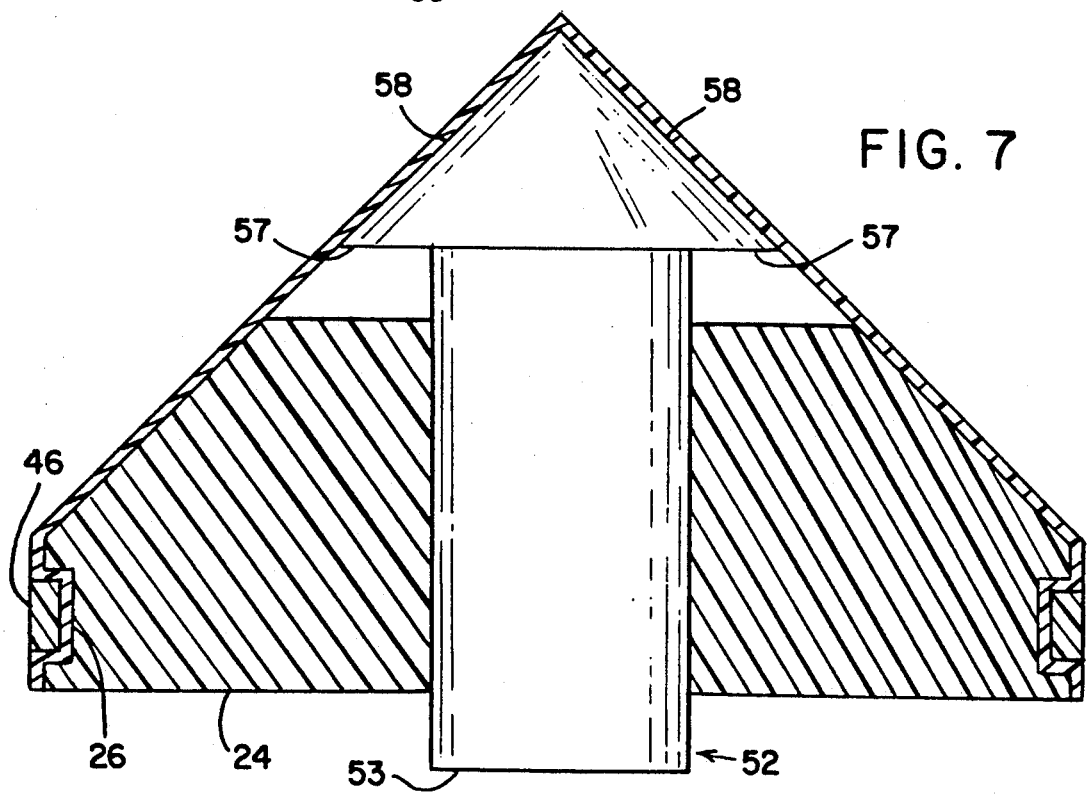
FIG. 7 is a cross-sectional elevational view of the assembled aspirating plunger in a dynamic bleed-aspirate configuration.

When force is exerted on plunger shaft 53 in a vertical upward direction, the shape of diaphragm-shell 44 is altered to conform to that shown in FIG. 7: the application of the force results in elastic deformation of the diaphragm-shell.

When exertion of force is partially or completely removed from plunger shaft 53, the elastic memory of diaphragm-shell 44 will urge the male component 50 back to its original position shown in FIG. 6. As male component 50 returns to its static position, negative gauge pressure is generated in the closed system, thereby drawing blood or body fluid into the power injector cartridge.

The aspirating plunger of the present invention is shown in position within a power injector cartridge denoted at 1 in FIGS. 8 and 9. Not shown in the assembly is a butterfly needle or equivalent to make the appropriate interface with a patient for the administration of a liquid formulation/biological agent, such as an imaging medium or a medicament. Such connecting implements are well known in the art. Also not shown is the power injector to which the cartridge is attached or in conjunction of which it is used. However, power injectors are also known in the art. After the pre-filled cartridge is ready for use and appropriate interface is made with the patient, the cartridge must be aspirated to assure that the desired blood vessel has been penetrated. As also described with respect to FIG. 6, pressure applied on plunger shaft 53 in the cartridge by the power injector (FIG. 8) in the direction of tip 2 of cartridge 1 forces diaphragm-shell 44 towards the distal end of the cartridge expelling head gas from the cartridge (FIG. 9). During application of force, cylindrical wall 42 of diaphragm-shell 44 maintains a tight seal between it, and the wall of barrel 3 of cartridge 1 without movement. Upon releasing pressure applied on plunger shaft 53, diaphragm-shell 44 returns male component 50 to its static position, thereby creating a vacuum in barrel 3 and drawing body fluid from the patient.

To inject the liquid contained in the cartridge after the aspirating process has been completed, a continuous steady force is applied to plunger shaft 53 to displace the liquid from the cartridge and deliver it to the patient. It is critical to the function of the aspirating plunger/cartridge assembly that the force needed to overcome the frictional drag between cylindrical wall 42 of diaphragm-shell 44 and barrel 3 is greater than the force required to elastically deform diaphragm-shell 44.

It will be appreciated from the foregoing description that the aspirating plunger of the instant invention possess all the attributes of an ideal aspirating plunger as enumerated above. That is, the plunger is simple in construction, thus minimizing the cost of production; it is simple to operate; it is capable of manipulation with one hand; it is capable of multiple self-aspirating actions with each cartridge ampoule; and it is capable of expelling air trapped within the ampoule either prior to initiation of the self-aspirating action or at any time during the sequence of actions necessary for injection of the ampoule content without, on the one hand, precluding self-aspirating action at any point in the sequence or, on the other, rendering the self-aspirating action inoperative.

Having thus described the invention and the advantages thereof, it is considered that the invention is to be broadly constructed and limited only by the following claims.

What is claimed is:

1. In a self-aspirating hypodermic cartridge which contains an injectable fluid therein including a generally cylindrical barrel having a wall, and a plunger reciprocable in said barrel to aspirate the cartridge and to expel said injectable fluid therefrom wherein the improvement comprising: the plunger having a female ring component, with a vertically oriented cylindrical hole, having a cylindrical flat bottom portion, a cylindrical flat top portion spaced from said cylindrical flat bottom portion, and a side portion connecting said cylindrical bottom and top portions and integral therewith, said side portion having a degree of incline with respect to a horizontal plane of from about 1° to about 89°;

a mushroom-shaped component having a cylindrical plunger shaft slideably positioned into said female ring component, and a cone-shaped head at one end of the shaft and integral therewith having a degree of incline with respect to a horizontal plane of from about 1° to about 89°; and an elastomeric diaphragm-shell having a cylindrical bottom portion and a generally cone-shaped side portion integral therewith covering said male and female components, said cylindrical bottom portion forming a slideable seal between the female ring component and the wall of the cylindrical barrel when the plunger is placed in the barrel and said cone-shaped side portion forming a diaphragm whereby upon alternate exertion of pressure upon said plunger shaft and release thereof the deformation of the diaphragm reduces head space in the cylindrical barrel thereby expelling head space gas and upon release of pressure the diaphragm returns to its original shape resulting in aspiration.

2. The self-aspirating hypodermic cartridge of claim 1 wherein said cylindrical flat bottom portion of said female ring component further comprises a cylindrical groove, and said cylindrical bottom portion of said elastomeric diaphragm-shell further comprises an inwardly protruding protuberance to engage said cylindrical groove on said female ring component.

3. The self-aspirating hypodermic cartridge of claim 1, wherein the force needed to expel said injection fluid from said barrel exceeds the force required to aspirate said hypodermic cartridge.

4. The self-aspirating hypodermic cartridge of claim 1, wherein said side portion of said female ring component forms about a 45° incline with respect to a horizontal plane.

5. The self-aspirating hypodermic cartridge of claim 1, wherein said cone-shaped head of said male component forms about a 45° incline with respect to a horizontal plane.

6. The self-aspirating hypodermic cartridge of claim 1 wherein said male component and said female component are of rigid polymeric material.

* * * * *